(12) United States Patent
Vieth et al.

(10) Patent No.: US 9,999,602 B2
(45) Date of Patent: Jun. 19, 2018

(54) LIQUID MENTHOL COMPOSITIONS

(71) Applicant: DDROPS COMPANY, Woodbridge, Ontario (CA)

(72) Inventors: Simon George Vieth, Toronto (CA); Chris James Temovsky, Kleinburg (CA); Reinhold William Vieth, Toronto (CA)

(73) Assignee: DDROPS COMPANY, Woodbridge, Ontario (CA)

( * ) Notice: Subject to any disclaimer, the term of this patent is extended or adjusted under 35 U.S.C. 154(b) by 0 days. days.

(21) Appl. No.: 14/762,730

(22) PCT Filed: Jan. 31, 2014

(86) PCT No.: PCT/CA2014/000090
§ 371 (c)(1),
(2) Date: Jul. 22, 2015

(87) PCT Pub. No.: WO2014/117265
PCT Pub. Date: Aug. 7, 2014

(65) Prior Publication Data
US 2015/0359753 A1 Dec. 17, 2015

Related U.S. Application Data

(60) Provisional application No. 61/759,839, filed on Feb. 1, 2013.

(51) Int. Cl.
| | | |
|---|---|---|
| *A61K 31/045* | (2006.01) | |
| *A61K 47/14* | (2017.01) | |
| *A61K 9/08* | (2006.01) | |
| *A61K 45/06* | (2006.01) | |
| *A61K 31/593* | (2006.01) | |
| *A61K 47/44* | (2017.01) | |
| *A61J 1/14* | (2006.01) | |

(52) U.S. Cl.
CPC ........... *A61K 31/045* (2013.01); *A61J 1/1475* (2013.01); *A61K 9/08* (2013.01); *A61K 31/593* (2013.01); *A61K 45/06* (2013.01); *A61K 47/14* (2013.01); *A61K 47/44* (2013.01)

(58) Field of Classification Search
CPC .............. A61K 31/045; A61K 2300/00; A61K 31/593; A61K 45/06; A61K 47/14; A61K 47/44; A61K 9/08; A61J 1/1475
See application file for complete search history.

(56) References Cited

U.S. PATENT DOCUMENTS

| | | | | |
|---|---|---|---|---|
| 5,858,382 A | * | 1/1999 | Magdassi | A61K 9/107 424/405 |
| 7,138,394 B2 | * | 11/2006 | Schwarz | A61K 9/0014 514/226.5 |
| 2006/0105000 A1 | * | 5/2006 | Friedman | A61K 9/0031 424/400 |
| 2008/0069925 A1 | * | 3/2008 | Vieth | A23D 9/007 426/72 |

FOREIGN PATENT DOCUMENTS

| | | | | |
|---|---|---|---|---|
| CA | 2258513 | | 1/1998 | |
| CA | 2 558 202 | | 11/2006 | |
| CA | 2 711 703 | | 7/2008 | |
| CA | 2 745 267 | | 1/2013 | |
| EP | 1 640 022 | | 3/2006 | |
| EP | 1640022 A1 | * | 3/2006 | ........... A61K 9/1075 |
| WO | 00/37044 | | 6/2000 | |
| WO | 2004/045572 | | 6/2004 | |

OTHER PUBLICATIONS

Written Opinion issued in PCT/CA2014/000090, dated May 16, 2014, pp. 1-7.
International Search Report issued in PCT/CA2014/000090, dated May 16, 2014, pp. 1-3.
Paul, et. al., "vapor rub, petrolatum and no treatment for children with nocturnal cough and cold symptoms," Pediatrics, 126 (2010), pp. 1092-1099.
Krishna, et. al., "coconut oil: chemistry, production and its applications—a review", Indian Coconut Journal, Jul. 2010 (Jul. 2010), pp. 15-27.

* cited by examiner

*Primary Examiner* — Sreeni Padmanabhan
*Assistant Examiner* — Jody Karol
(74) *Attorney, Agent, or Firm* — Jeffrey S. Melcher; Manelli Selter PLLC

(57) ABSTRACT

A composition is provided comprising: (i) menthol, and (ii) a carrier comprising a digestible edible oil, wherein said digestible edible oil is one that provides a composition which is a liquid at 20° C. after rising to that temperature from a lower temperature at which the oil was previously semisolid. The preferred edible oil is a medium-chain triglyceride oil, wherein the level of menthol in the composition is between 1-50% by total weight, so as to provide an menthol application rate of between 5 and 20 mg of menthol, and most preferably, about 10 mg menthol, in a single droplet of the composition. The composition can also include additional added vitamins and essential oils. A liquid method for administering menthol is provided.

16 Claims, No Drawings

LIQUID MENTHOL COMPOSITIONS

FIELD OF THE INVENTION

The present invention is a composition of matter suitable for administering liquid menthol in liquid form, and in particular, for the administration of liquid menthol in a drop form.

BACKGROUND OF THE INVENTION

Menthol is known as an essential oil, because its vapours have an aromatic "essence". The taste and smell of menthol is pleasant and it offers relief from symptoms of colds or flu [1 Paul I M, Beiler J S, King T S, et al. Vapor Rub, Petrolatum, and No Treatment for Children with Nocturnal Cough and Cold Symptoms. Pediatrics 2010; 126(6):1-8.]. Many products for administering essential oils incorporate combinations of essential oils that include menthol and are for topical use. Usually topically applied products comprising of menthol in an oil base are semisolid at ambient temperature. An example of such a product is Vics Vapo-Rub®.

U.S. Pat. No. 7,138,394 [Schwarz and Welsspapir] teaches the use of a composition for topical delivery of non-steroidal analgesic cream medication that comprises among its ingredients menthol together with camphor and medium chain triglyceride (MCT). This mixture is a semisolid at room temperature. Solubilization of the non-steroidal analgesic in the topical cream was accomplished with the use of medium-chain triglyceride along with the combination of menthol and camphor. Semisolid products and creams do not lend themselves to accurate measurement of the amount of compound used or applied.

Menthol is also commonly used as a component of cold remedies that are ingested orally. One example is a group of products marketed under the brand name Halls®. These are typically packaged as wrapped, hard-candy-lozenges. These lozenges contain as their therapeutic dose as much as 10 mg menthol each. One of these products includes among its ingredients MCT, Halls Mountain Berry with Soothing Honey Center (Active ingredient: Menthol 2.5 mg. Inactive ingredients: citric acid; cottonseed oil; elderberry juice; flavors; ginger; glucose syrup; glycerin; honey; lemon grass; MCT oil; sage; soy lecithin; sucrose; water; white thyme).

A review conducted by the Federeal Drug Administration (FDA) in the United States concluded that the dose of menthol required for antitussive (i.e., cough-suppressant) effect is at least 5 mg [Federal Register/Vol 52, No. 155/ Wednesday, Aug. 12, 1987, page 39946]. Liquid products for the treatment of cough are generally in a syrup form and contain menthol as a therapeutically active agent in the dose range of 5-20 mg per dose, with each dose provided in the general volume of a spoonful (5 mL). An example of such a product is Buckley's Mixture®. The liquid oral preparations containing menthol are water-based syrups, which necessitates the inclusion of solublilizers that keep the menthol in the liquid phase.

Pure menthol is solid at ambient temperature, with a melting point of 42 degrees Centigrade. Menthol is poorly soluble in water-based preparations, but it is readily dissolvable at high concentration in alcohol. Menthol is also soluble in oils, including MCT. However, at higher concentrations, these solutions are often semisolid and waxy at ambient temperature (18-23° C.). Moreover, as will be discussed hereinbelow, these oil formulations typically exhibit a temperature hysteresis effect that normally mitigates their use for administration of a liquid menthol composition.

Further, among the difficulties associated with the prior art approaches to the use of menthol are that many of the products are semisolid and are suitable only for topical application, or for inhalation. Semisolid preparations are not suitable for oral use because they cannot be measured reliably. As such, because of their tendency to be semisolid, waxy or ointment-like, preparations of menthol in oil are used for topical application to the skin.

Often these products are added to a vaporizer and they are not for oral use, because the magnitude of an oral dose must be obtainable by means that are simple, accurate and reliably dispensed. Other menthol products are in the style of confectionaries, or menthol is present as one component of conventional bad-tasting cough syrup that needs to be administered by the spoonful.

Available through the internet are other unspecified liquid menthol products of unspecified concentration, and which some persons use to add menthol to cigarettes.

Additionally, one alternative recipe for a menthol product, is to dissolve two volumes of menthol crystals in one volume ethanol (http://nu-vapor.com/forum/diy-liquids/1604-diy-menthol-drops-make-your-own.html). The difficulty with this kind of product is the unreliable nature of ethanol, which is volatile, and hence results in an unreliable concentration of menthol that is influenced by the amount of ethanol evaporation occurring over time. As alcohol evaporates with storage, the concentration of menthol will eventually reach a sufficiently elevated level to cause solidification.

Water-based menthol preparations are commonly available, but of necessity, are relatively dilute and typically require the consumption of at least 1 teaspoon-full of liquid.

Alternatively, Tonori et al [EP1640022 A1] teach that MCT is useful for dissolving menthol in a range of 0.5- to 10-fold by weight. However, his technique requires preparation of the composition by heating to 80° C. and then emulsification of the mixture to prepare a menthol-containing emulsion. The composition described by Tonori et al was used to provide an L-menthol emulsion in a fat or oil together with water and a surfactant to be used during endoscopic surgery to inhibit contraction of the digestive tract. The Tonori et al patent does not disclose anything about the solidification behaviors of menthol in MCT and offers no insight as to the suitability of a liquid menthol composition for use as a liquid cough suppressant.

As such, there exists no product suitable for the mainstream drug-store market that provides a way to provide a concentrated liquid solution of menthol in a manner that makes it possible to obtain a therapeutic dose (about 5-20 mg menthol) in one or two drops of liquid.

Such a product, if currently available, would have a broad appeal over a wide variety of consumer ages.

However, although menthol is a liquid oil when it is above 42° C., and is soluble in oil, the goal of a meaningful dose of menthol in a single drop of oil has remained problematic. The greatest difficulty is that if the menthol product becomes semisolid, it is useless for oral consumption unless reheated to a higher temperature.

Accordingly, there is a need in the art for a non-alcoholic, non-water-based, liquid menthol product that provides a consistently reproducible therapeutic dose and that returns to liquid at room temperature, (e.g. 18-23° C.), even after having been previously solidified at a lower temperature, which would be expected to occur during regular transport or storage.

Also preferred, would be a product suitable for administration by means of dispensing preferably one single drop accurately and reliably.

As such, to overcome the difficulties of the prior art, it would be advantageous to provide a liquid menthol composition that would be suitable for administration as a liquid material, and more preferably, to provide a liquid menthol composition for administration in a droplet form.

Accordingly, it would advantageous to provide a liquid menthol composition which would obviate or mitigate at least one of the above-mentioned disadvantages of the prior art.

Further, it would also be an advantage of the present invention to provide a novel composition that is useful as a medication to alleviate the symptoms of colds or flu.

SUMMARY OF THE INVENTION

The advantages set out hereinabove, as well as other objects and goals inherent thereto, are at least partially or fully provided by the liquid menthol compositions and solutions of the present invention, and their use, as set out herein below.

Accordingly, in one aspect, the present invention provides a composition comprising of menthol dissolved in medium-chain triglyceride oil. More preferably, the present invention provides a composition comprising: (i) menthol, and (ii) a carrier comprising a digestible edible oil, wherein said digestible edible oil is one that provides a composition which is a liquid at 20° C. after rising to that temperature from a lower temperature at which the oil was previously semisolid.

Preferably, the digestible edible oil is a medium chain triglyceride.

In another of its aspects, the present invention relates to use of the above-mentioned composition as cold remedy to be taken orally or topically or inhaled. In another of its aspects, the present invention relates to use of the above-mentioned composition as a flavoring for food and in recipes.

In yet another of its aspects, the present invention incorporates a delivery system for dispensing the above-mentioned composition.

In yet another of its aspects, the present invention relates to use of the above-mentioned delivery system to dispense the above-mentioned composition as a cough and cold remedy.

In yet another aspect of the present invention, there is provided a composition comprising menthol in a solution of edible oil, which composition is provided in a vial that is capped with a dropper, and preferably a vertical-dropper dispenser plug which is commercially available as a Euro-dropper.

In yet another aspect of the present invention, there is provided a method for delivering menthol by the consumption of the liquid menthol and oil composition of the present invention. This is preferably done by consumption of one or two drops of the composition, which can be achieved by consumption of the liquid from an exterior surface. This technique can include practices such as licking one or two dispensed drops from the back of a hand or spoon, or the like. However, other consumption techniques are not excluded.

DESCRIPTION OF THE PREFERRED EMBODIMENTS

In the development of the present invention, it was noted that although oils, in general, can dissolve menthol, the major problem that needed to be overcome was that oils readily become semisolid in the presence of menthol. Even if they are initially liquid at room temperature (e.g. approximately 18-23° C.), once oils containing high concentrations of menthol cool below room temperature they can turn irreversibly semisolid. This can happen if the menthol oil solutions are refrigerated or exposed to winter temperatures during the season in which coughs and colds occur most frequently. This temperature based hysteresis makes most oil-based menthol products unsuitable for dispensing as an oral dose, because semisolids are difficult to measure accurately. Although it is possible to re-liquefy solutions of menthol in oil by re-heat them, the need for special treatment of product by customers is highly unsuitable for products intended for sale in the mass-market served by conventional drugstores, food and mass retailers.

As such, as a result of this temperature hysteresis, the transition temperature between the liquid-to-semisolid state (i.e., freezing) of menthol-in-oil preparations differs from the transition temperature from the semisolid-to-liquid state (i.e., melting). That is, the transition temperature differs, depending on whether the preparation reaches ambient temperature after being at a low temperature, when compared to its transition temperature when returning to ambient temperature after being at a warmer temperature.

This hysteresis phenomenon is therefore characterized by state transitions where the melting temperature and freezing temperatures are different.

Preferred edible oils that can dissolve menthol can include oils such as MCT, corn oil, peanut oil, sunflower oil, canola oil, and the like. Most preferably, the edible oil is a medium chain triglyceride, since these MCT oils exhibit the least amount of temperature based hysteresis.

Medium chain triglyceride (MCT) oils are preferably isolated from vegetable oil by distillation. The medium chain triglycerides of use in the practice of the invention preferably have carbon-chain lengths of 6-12 and, preferably, the composition medium comprises at least 95% triglycerides having a carbon-chain length selected from 8-10. Medium-chain triglycerides are preferably obtained from the oil extracted from the hard, dried fraction of the endosperm of *Cocos nucifera L.* or from the dried endosperm of *Elaeis guineensis Jacq.* They typically consist of a mixture of triglycerides of saturated fatty acids, mainly of caprylic acid (C8I-11602) and of capric acid (C101-12002). Preferred oils contain not less than 95% of saturated fatty acids having 8 to 10 carbon atoms, and preferably, the oil is a clear solution.

According to the preferred embodiment of the present invention, the level of menthol in the oil and menthol composition, and preferably in the MCT and menthol composition, is between 1 and 50%, by weight. More preferably, the level of menthol in the oil and menthol composition is between 10 and 48.7%, and more preferably, 15 to 48.7%, by weight. Even more preferred, the level of menthol in the oil and menthol composition is between 29.5 and 42.5%, and more preferably, at a level of between 25 to 30%, by weight.

Alternatively, in other formulations, the level of method in the menthol and oil compositions is between 5 and 15%, by weight, and more preferably between 5 and 42.3% by weight.

The dose of menthol can be dispensed as one single drop of oil solution that provides between 5 and 20 mg of menthol, and most preferably, about 10 mg menthol.

In the practise of the present invention, the composition is preferably administered as a single drop of liquid to be consumed by the user. We have found that a Eurodropper bottle will reliably deliver at least 10 mg of menthol in a single drop (about 28 mg of liquid).

As such, in a further aspect, the present invention further provides an article of manufacture comprising a packaged article comprising a preferably glass vial capped with a Eurodropper, and a composition contained therein, wherein said composition is a liquid menthol solution, as herein described, so as to effectively to treat a cough and/or cold. Preferably, the packaged article comprises a vial into the opening of which is inserted a Eurodropper fitting to dispense individual drops, and a screw cap to completely enclose the contents.

The composition preferably comprises menthol dissolved in medium chain triglyceride oil.

The present composition advantageously provides menthol in a form that is easily administered to a human. When taken directly by mouth or licked or inhaled from a surface, the composition has a desirable flavor and is easy to consume. Moreover, the high concentration of menthol per unit volume of the composition results in a minimal volume of liquid to be administered to achieve the desirable therapeutic effect.

The present composition can also include one or more fat-soluble vitamins, including, for example, vitamin A, vitamin E, carotene, lycopene, lutein, vitamin D, or vitamin K.

Also, the composition of the present invention can also include one or more essential oils. These essential oils can include camphor oil, lavender oil, rose oil, eucalyptus oil, tea tree oil, ginger oil, peppermint, spearmint oil, cinnamon oil, oregano oil, frankincense, myrrh, cinnamon oil, wintergreen, camomil, orange oil, lemon oil.

However, the addition of other vitamins and essential oils is not excluded.

The composition can be used as a remedy in the treatment of coughs, or symptoms of colds, or in the treatment of coughs, or symptoms of colds with or without symptoms of flu.

The composition is normally intended to be consumed by sucking or licking the a droplet of material from a surface, such as the user's skin, or the droplet can be administered directly into the mouth of the user.

Alternatively, the present invention can be used by inhalation, for the treatment of coughs, or symptoms of colds, with or without symptoms of flu.

The compositions of the present invention can also be used as a topical treatment, in the treatment of, for example, local pain or insect bites.

In yet another feature, the present invention provides an article of manufacture comprising a packaged article, preferably as a glass or squeezable plastic vial, with the composition of the present invention contained therein. The packaged article thus contains a pharmaceutical composition contained therein, wherein said pharmaceutical composition is therapeutically effective to treat the symptoms of the common cold. Preferably, the packaging material comprises capped vial from which the menthol solution is drawn up using a calibrated eyedropper or a syringe.

Alternatively, the packaging material is a plastic vial capped with a nozzle having an aperture, whereby the vial can be inverted and drops from the aperture counted as they are squeezed from the vial.

Thus, the present inventors have discovered a composition that is particularly suitable for administration of menthol in a simple manner suitable for children and adults, and one feature of the present invention is that a liquid solution of the composition is provided that is suitable for administration as a droplet. Preferably, the droplet is provided by use of a Eurodropper, but alternatively, the present composition may be drawn up into a syringe or an eyedropper for administration, for example, to a mammal, and in particular, a human being. It has been discovered that solutions of menthol in medium-chain-triglyceride oil can be manufactured to provide a full therapeutic or pharmaceutical dose, being about 10 mg of menthol, per drop.

EXAMPLES

The advantages of the present invention will now be demonstrated by the following discussion. The examples described herein are for demonstration purposes only, and are non-limiting on the scope of the present invention.

Example 1—Determination of Menthol-In-Oil Phase Stability and Discovery of Phase Transition Temperature Hysteresis Phenomenon The menthol used was (1R, 2S, 5R)-5-menthol-2-(1-methylethyl)-cyclohexanol with a molecular weight of 156.27 and a melting point of 42° C. Crystalline menthol was combined with the various oils on a weight-per-weight basis and fully dissolved in each oil at 40° C. The percentages of menthol indicate the percent of menthol as a proportion of total weight of the preparation. Table 1 shows the state of each preparation of menthol with the various oils as they cooled down to 23° C. The term "solid" refers to a non-liquid, or at least semisolid composition, not pourable at room temperature and often exhibiting crystalization or other bi-phasic inhomogeneity. Of the various oils we tested, we found that menthol in medium chain triglyceride oil (MCT) remains liquid at room temperature up to 48.7% menthol, a higher concentration than all other oils. Canola oil was the next most suitable of those tested, which remained liquid at room temperature up to 35.9% menthol.

TABLE 1

State of Menthol in Oil after cooling from 40° C. to room temperature (23 C.)

| | % Menthol | | | | |
| --- | --- | --- | --- | --- | --- |
| | 29.5% | 35.9% | 42.3% | 48.7% | 55.1% |
| MCT | Liquid | Liquid | Liquid | Liquid | Solid |
| Corn | Liquid | Solid | Solid | Solid | Solid |
| Peanut | Liquid | Solid | Solid | Solid | Solid |
| Sunflower | Liquid | Solid | Solid | Solid | Solid |
| Canola | Liquid | Liquid | Solid | Solid | Solid |
| Glycerin | Solid | Solid | Solid | Solid | Solid |

The preparations of Table 1 were cooled to 4° C., which resulted in the solidification of all of the preparations except for the 29.5% menthol in MCT. Then, the preparations were returned to room temperature and allowed to stand for 12 hours. That produced the observations shown in Table 2, which remained at steady state as shown in the table for at least one week. Unexpectedly, the state of menthol-in-oil preparations at room temperature can differ depending on whether room temperature was achieved via heating or cooling. More specifically, it was found that the freezing temperature differs substantially from the melting temperature for a range of menthol-in-oil preparations.

Also discovered was that solid state menthol in oil preparations, upon being returned to room temperature, do not instantaneously return to the liquid state. This represents an unpredictable behaviour of product that is highly undesirable in the hands of a consumer. A commercially viable liquid menthol product must exhibit predictable liquid behaviour at a specified temperature. Rapid melting, for example within 5 minutes, will ensure the preparation can be dispensed essentially on-demand so long as it is at room temperature (e.g. 20° C.). Slow melting, however, will require the product be held longer at 20° C. before dispensing or be held at a higher temperature.

A preparation of canola oil with menthol was prepared. 1.5 grams of menthol was dissolved into 8.5 grams of canola at 40° C. until the preparation was observed to have a single, liquid phase. A similar preparation of menthol in MCT was also prepared. The samples were held at 4° C. until any phase changes had completed; MCT-menthol remained liquid, whereas canola-menthol solidified. Both samples were then returned to 20° C. and the rate of phase change was observed. MCT-menthol remained liquid across the temperature range investigated. After 5 minutes, the canola-menthol preparation remained predominantly solid and indispensible via a dropper. After 10 minutes the sample returned to a predominantly liquid state yet still exhibited solid crystals which would impair drop-wise dispensability and dose consistency. After 15 minutes the canola-menthol preparation was fully liquid.

While 15% menthol in MCT remained liquid and dispensable across the range of temperatures investigated, menthol in canola exhibited a phase transition time of 15 minutes prior to reaching a dispensable steady state.

TABLE 2

State of Menthol in Oil from 4° C., warmed to room temperature (23° C.) for 24 hrs

| | % Menthol | | | | |
|---|---|---|---|---|---|
| | 29.5% | 35.9% | 42.3% | 48.7% | 55.1% |
| MCT | Liquid | Liquid | Liquid | Solid | Solid |
| Corn | Solid | Solid | Solid | Solid | Solid |
| Peanut | Solid | Solid | Solid | Solid | Solid |
| Sunflower | Solid | Solid | Solid | Solid | Solid |
| Canola | Solid | Solid | Solid | Solid | Solid |
| Glycerin | Solid | Solid | Solid | Solid | Solid |

Of special note, it was discovered that menthol solution in MCT oil exhibited uniquely desirable characteristics, whereby it remained liquid at room temperature through a broader range of menthol percentages, even after having been previously solidified at 4° C. For example, while a 29.5% preparation of menthol-in-oil was liquid at room temperature, 23° C., for both MCT and canola oil when arrived at via cooling, the same canola oil preparation was solid when room temperature was arrived at via heating.

Example 2—Elucidation of Phase Transition Temperature Hysteresis in Preparations of Menthol-In-Oil Menthol-in-oil solutions were prepared at concentrations of 20%, 25% and 30% menthol (as a percentage of total preparation weight) in MCT, corn, canola, sunflower and peanut oils. Solutions were held at 40° C. to ensure complete dissolution of menthol in the oils. Samples were then placed in a temperature-controlled incubator and temperatures were decreased step-wise by 2° C. decrements (from 40° C. to 2° C.), holding the samples for 12 hours between decrements. Samples were observed after each holding period to determine if phase transition (from liquid to solid) had taken place. The resulting freezing points are shown in TABLE 3, below.

TABLE 3

Freezing point for menthol-in-oil preparations across a range of menthol concentrations (w/w %)

| | 20% | 25% | 30% |
|---|---|---|---|
| MCT | <2° C. | <2° C. | 4° C. |
| Corn | 6° C. | 8° C. | 14° C. |
| Canola | 6° C. | 12° C. | 14° C. |
| Sunflower | 6° C. | 12° C. | 14° C. |
| Peanut | 6° C. | 8° C. | 14° C. |

For example, a preparation of 30% menthol in canola oil (w/w %) will solidify when cooled down to 14° C. A preparation of 30% menthol in MCT (w/w %) will solidify at 4° C. Samples were then allowed to rest at 2° C. for >24 hours to allow all phase transitions to reach equilibrium. Temperature incrementing then commenced in a fashion similar to the above-mentioned temperature declination experiments (i.e., 2° C. increases with 12 hour holding periods). Samples were observed after each holding period to determine if phase transition (from solid to liquid) had taken place. The resulting melting points are shown in TABLE 4, below.

TABLE 4

Melting point for menthol-in-oil preparations across a range of menthol concentrations (w/w %)

| | 20% | 25% | 30% |
|---|---|---|---|
| MCT | <2° C. | <2° C. | 12.5° C. |
| Corn | 16.5° C. | 23° C. | 26° C. |
| Canola | 16.5° C. | 23° C. | 26° C. |
| Sunflower | 16.5° C. | 21° C. | 26° C. |
| Peanut | 16.5° C. | 21° C. | 26° C. |

For example, a preparation of 30% menthol in canola oil (w/w %) is solid at 4° C. and it will become liquid once it reaches 26° C. A preparation of 30% menthol in MCT (w/w %) will become liquid once it reaches 12.5° C.

Phase transition temperature hysteresis results were then calculated and are presented in TABLE 5 with the understanding the a smaller value for phase transition temperature hysteresis is generally preferred to a larger one from a commercialization perspective. This stems from the need for product that, in order to be commercially viable, must withstand cold, solidifying temperatures and then return to a liquid state without the need for treatment at temperatures higher than room temperature.

TABLE 5

Phase transition temperature hysteresis (i.e., Tmelting-Tfreezing) for menthol-in-oil preparations across a range of menthol concentrations (w/w %)

| | 20% | 25% | 30% |
|---|---|---|---|
| MCT | N/A | N/A | 8.5° C. |
| Corn | 10.5° C. | 15° C. | 12° C. |
| Canola | 10.5° C. | 11° C. | 12° C. |
| Sunflower | 10.5° C. | 9° C. | 12° C. |
| Peanut | 10.5° C. | 13° C. | 12° C. |

For example, a preparation of 30% menthol in canola oil (w/w %) exhibits a melting point (26° C.) that is 12° C. higher than its freezing point (14° C.). A preparation of 30% menthol in MCT (w/w %) exhibits a melting point (12.5° C.) that is 8.5° C. higher than its freezing point (4° C.).

Example 3—Drop-Wise Dispensability of Pharmacologically and Commercially Desirable Preparation of MCT and Menthol Thirty-five grams of crystalline menthol was melted at 43 degrees Centigrade and mixed into 65 grams of medium-chain triglyceride. Ten milliliters was dispensed into a 15-milliliter amber-glass vial which was fitted with a Euro-dropper cap. The screw cap was removed, and one drop was dispensed directly onto the tongue.

Example 4—Drop-Wise Delivery of Pharmacologically and Commercially Desirable Dose of Menthol Thirty-five grams of crystalline menthol were melted by warming to 43 degrees Centigrade and the liquid menthol was mixed into 65 grams of medium-chain triglyceride oil, and allowed to cool to room temperature. Ten milliliters of the solution of menthol in MCT was dispensed into a 15-milliliter amber-glass vial, which was fitted with a Euro-dropper cap. The screw cap was removed, and the vial was inverted to allow five drops of the solution to be sampled for testing according to United States Pharmacopea methodology. The result of the testing showed that each drop of the composition provided 10 milligrams of menthol.

Example 5—Drop-Wise Consistency of Menthol-In-Oil Preparation Via an Integral Euro-Style Passive Displacement Dropper Thirty-five grams of crystalline menthol were melted by warming to 43 degrees Centigrade and the liquid menthol was mixed into 65 grams of medium-chain triglyceride oil, and allowed to cool to room temperature. Ten milliliters of the solution of menthol in MCT was dispensed into a 15-milliliter amber-glass vial, which was fitted with a Euro-dropper cap. The screw cap was removed, and the vial was inverted to dispense one drop onto a weigh scale. The vial was recapped and placed upright for one minute. The procedure to dispense, weigh and recap was repeated a total of 50 times. The drop weight was found to be 27.4±0.3 mg (mean±standard deviation). In comparison, drop weight of a 35% menthol in corn oil preparation was 29.7±1.1 mg, or 3.8 times more variable than MCT drops.

Example 6—Drop-Wise Delivery of Menthol-In-Oil Preparation With Added Essential Oils and Vitamins Twenty grams of crystalline menthol was dissolved into 80 grams of MCT at 43° C. To this preparation was added 10 grams of eucalyptus oil and sufficient vitamin D3 (Cholecalciferol) to yield a concentration of 345 micrograms per milliliter. Ten milliliters of the solution was dispensed into a 15-milliliter amber-glass vial, which was fitted with a Eurodropper cap. The screw cap was removed, and the vial was inverted to dispense one drop onto a weigh scale. The vial was recapped and placed upright for one minute. The procedure to dispense, weigh and recap was repeated a total of 50 times. The procedure was repeated as well with a 20% preparation of menthol in MCT, absent of added essential oils and vitamins. Both types of preparations exhibited virtually the same drop weights and consistency of drop weights. This indicated that the presence or absence of essential oils or other dissolved additives, such as vitamins, did not influence the behaviour of the preparation.

Thus, it is apparent that there has been provided, in accordance with the present invention, a liquid menthol composition which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps. Further, the invention illustratively disclosed herein suitably may be practiced in the absence of any element which is not specifically disclosed herein.

Moreover, words such as "substantially" or "essentially", when used with an adjective or adverb is intended to enhance the scope of the particular characteristic; e.g., substantially planar is intended to mean planar, nearly planar and/or exhibiting characteristics associated with a planar element.

Further, use of the terms "he", "him", or "his", is not intended to be specifically directed to persons of the masculine gender, and could easily be read as "she", "her", or "hers", respectively.

Also, while this discussion has addressed prior art known to the inventor, it is not an admission that all art discussed is citable against the present application.

The invention claimed is:
1. A single, liquid phase composition consisting of:
   (i) 5-42.3% menthol by total weight, and
   (ii) a digestible oil, wherein said digestible oil is a medium-chain triglyceride so that said composition is a liquid at 20° C. after rising to that temperature from a temperature of 4° C.
2. The composition as claimed in claim 1, wherein the % menthol in medium-chain triglyceride is 29.5-42.3%, by total weight.
3. The composition as claimed in claim 1, wherein the % menthol in medium-chain triglyceride is 25-30% by total weight.
4. The composition as claimed in claim 1, wherein a single drop of about 28 mg of the liquid composition, contains about 10 mg of menthol.
5. A single, liquid phase composition consisting of:
   (i) 5-42.3% menthol by total weight,
   (ii) a digestible oil, wherein said digestible oil is a medium-chain triglyceride so that said composition is a liquid at 20° C. after rising to that temperature from a temperature of 4° C., and
   (iii) at least one or more fat-soluble vitamins or one or more essential oils.
6. The composition as claimed in claim 5, wherein said vitamins are vitamin A, vita min E, carotene, lycopene, lutein, vitamin D, or vitamin K, or wherein said essential oils are camphor oil, lavender oil, rose oil, *eucalyptus* oil, tea tree oil, ginger oil, peppermint, spearmint oil, cinnamon oil, oregano oil, frankincense, myrrh, cinnamon oil, wintergreen, camomil, orange oil, or lemon oil.

7. A packaged article comprising menthol dissolved in medium chain triglyceride as claimed in claim 1, wherein said composition is provided in a bottle suitable for dispensing one drop at a time.

8. The packaged article as claimed in claim 7, comprising menthol dissolved in medium-chain triglyceride, in a bottle fitted with an aperture suitable for dispensing one drop at a time.

9. The packaged article as claimed in claim 8, comprising menthol dissolved in medium-chain triglyceride, and a glass bottle fitted with a Eurodropper dispenser, for dispensing one drop at a time.

10. The packaged article as claimed in claim 7, comprising menthol dissolved in medium-chain triglyceride, in a plastic squeeze bottle fitted with an aperture suitable for dispensing one drop at a time.

11. The packaged article as claimed in claim 7, comprising menthol dissolved in medium-chain triglyceride, in a bottle accompanied by an eyedropper suitable for dispensing one drop at a time.

12. A composition for use as a remedy in the treatment of coughs, or symptoms of colds, with or without symptoms of flu, wherein said composition consisting essentially of:
   (i) 5-42.3% menthol by total weight;
   (ii) a digestible oil; and
   (iii) optionally one or more fat-soluble vitamins, or one or more essential oils, wherein said digestible oil is a medium-chain triglyceride, so that said composition is a liquid at 20° C. after rising to that temperature from a temperature of 4° C.

13. The composition for use as claimed in claim 12, wherein said vitamins are vitamin A, vitamin E, carotene, lycopene, lutein, vitamin D, or vitamin K, or wherein said essential oils are camphor oil, lavender oil, rose oil, *eucalyptus* oil, tea tree oil, ginger oil, peppermint, spearmint oil, cinnamon oil, oregano oil, frankincense, myrrh, cinnamon oil, wintergreen, camomil, orange oil, or lemon oil.

14. The composition according to claim 1, wherein the composition is an oral composition in which between 5 and 20 mg of menthol can be present in a single drop and the composition is formulated to be taken directly by mouth, licked or inhaled from a surface.

15. The composition according to claim 5, wherein the composition is an oral composition in which between 5 and 20 mg of menthol can be present in a single drop and the composition is formulated to be taken directly by mouth, licked or inhaled from a surface.

16. The composition according to claim 12, wherein the composition is an oral composition in which between 5 and 20 mg of menthol can be present in a single drop and the composition is formulated to be taken directly by mouth, licked or inhaled from a surface.

* * * * *